(12) United States Patent
Förster

(10) Patent No.: US 8,636,508 B2
(45) Date of Patent: Jan. 28, 2014

(54) SELF-LIGATING BRACKETS FOR ORTHODONTICS

(76) Inventor: Rolf Förster, Pforzheim (DE)

( * ) Notice: Subject to any disclaimer, the term of this patent is extended or adjusted under 35 U.S.C. 154(b) by 0 days.

(21) Appl. No.: 13/132,857

(22) PCT Filed: Dec. 4, 2009

(86) PCT No.: PCT/EP2009/008690
§ 371 (c)(1),
(2), (4) Date: Aug. 3, 2011

(87) PCT Pub. No.: WO2010/063485
PCT Pub. Date: Jun. 10, 2010

(65) Prior Publication Data
US 2011/0318699 A1      Dec. 29, 2011

(30) Foreign Application Priority Data

Dec. 5, 2008 (DE) .......................... 10 2008 060 820

(51) Int. Cl.
*A61C 3/00* (2006.01)
(52) U.S. Cl.
USPC ............................................................ 433/10
(58) Field of Classification Search
USPC ...................................................... 433/10–15
See application file for complete search history.

(56) References Cited

U.S. PATENT DOCUMENTS

| 5,322,435 A | 6/1994 | Pletcher |
| 5,466,151 A * | 11/1995 | Damon ........................... 433/10 |
| 5,613,850 A | 3/1997 | Wildman et al. |
| 6,071,118 A | 6/2000 | Damon |
| 6,247,923 B1 * | 6/2001 | Vashi ............................... 433/10 |
| 7,419,375 B2 * | 9/2008 | Farzin-Nia et al. ............. 433/10 |
| 7,785,101 B2 | 8/2010 | Förster |
| 2002/0009689 A1 * | 1/2002 | Kim .............................. 433/60 |
| 2005/0181331 A1 * | 8/2005 | Lustig et al. ................. 433/173 |
| 2008/0113311 A1 | 5/2008 | Förster |
| 2010/0055637 A1 * | 3/2010 | Rodriguez et al. ............ 433/10 |
| 2011/0143301 A1 * | 6/2011 | Maijer et al. .................... 433/11 |

FOREIGN PATENT DOCUMENTS

| EP | 1679048 A2 | 7/2006 |
| WO | 99/40871 A1 | 8/1999 |
| WO | 2009/006286 A1 | 1/2009 |
| WO | 2009/015157 A1 | 1/2009 |

* cited by examiner

*Primary Examiner* — Eric Rosen
(74) *Attorney, Agent, or Firm* — Keith H. Orum; Orum & Roth, LLC

(57) ABSTRACT

Self-ligating bracket for orthodontics has a base, an occlusal wall extending from the base and occlusal ligature wing, a gingival wall extending from the base and gingival ligature wing, a slot, which separates the occlusal wall and the gingival wall from one another and extends continuously in the direction from mesial to distal, and a slide, which is held in a guide provided in the occlusal wall and/or in the gingival wall. The guide can be shifted in the gingival-occlusal direction, between a closed position, in which the slide bridges the slot, and a open position, in which the slot is open in labial direction. A structure holds the slide in its closed position as well as in its open position.

30 Claims, 12 Drawing Sheets

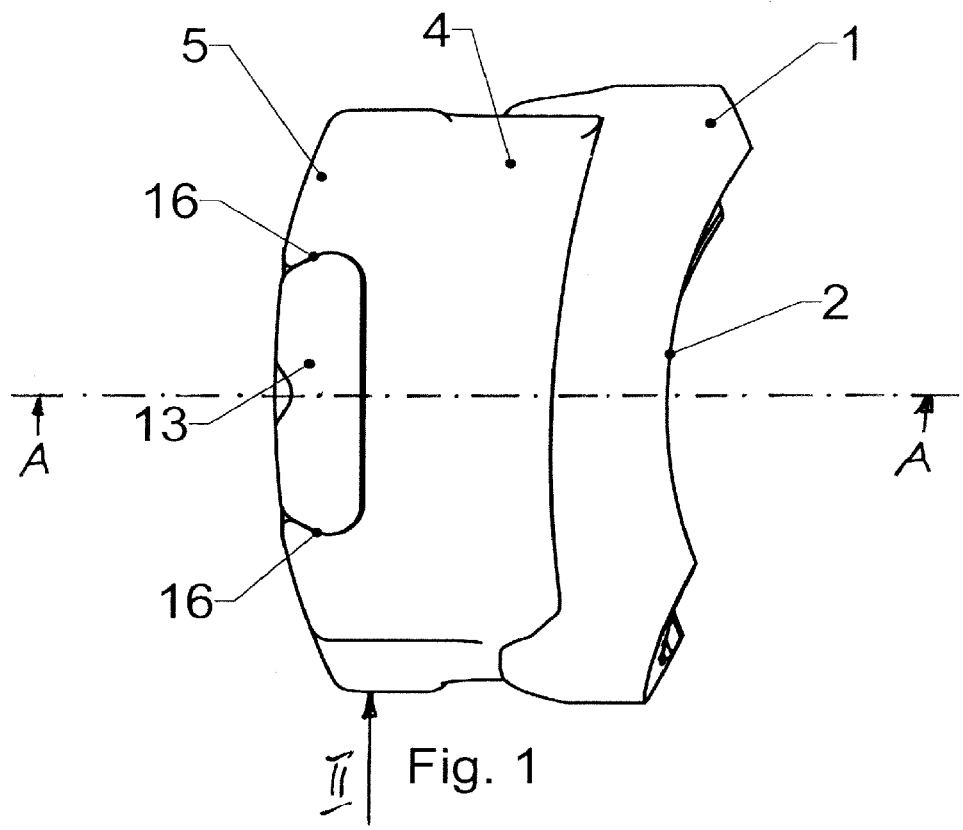
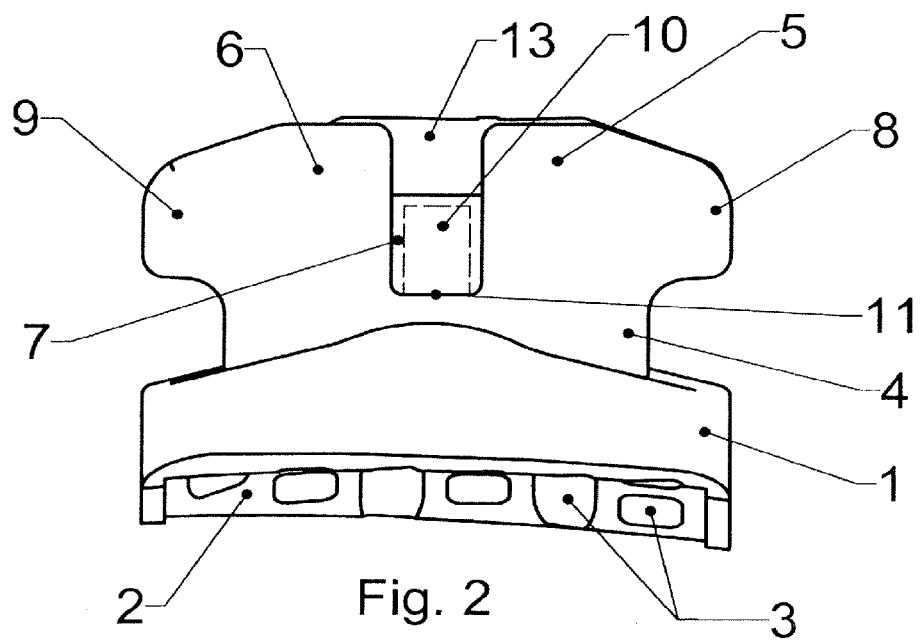

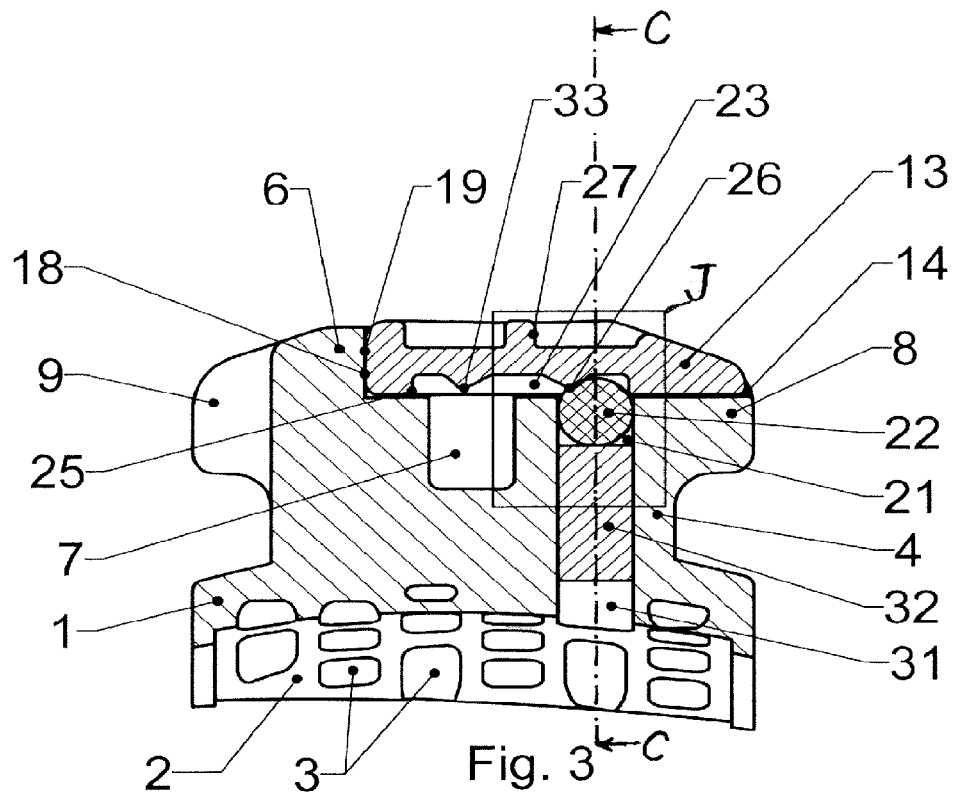
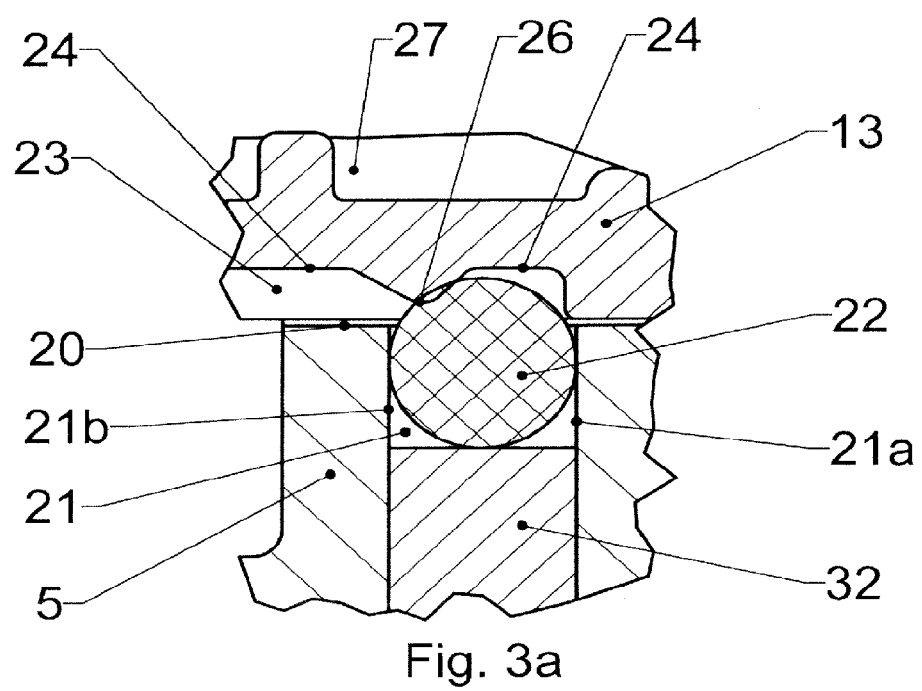
Fig. 3
Fig. 3a

SELF-LIGATING BRACKETS FOR ORTHODONTICS

BACKGROUND OF THE INVENTION

U.S. Pat. No. 5,322,435 A discloses a bracket which has a slide for closing its slot, which can be displaced in lateral guiding slots, which are provided in the occlusal wall as well as in the gingival wall of the bracket. In order to hold the slide in its closed position as well as in its open position, a bore open to the slide is provided in one of the walls of the bracket, in which either a helical spring, which presses against the underside of the slide, or a cylindrical bolt made of elastomeric synthetic material is situated, which protrudes over the opening of the bore and presses against the underside of the slide. Two recesses are provided on the underside of the slide. The spring respectively the bolt with its end protruding from the bore meshes into one of the recesses when the slide is in open position. The spring respectively the bolt with its end protruding from the bore meshes into the other recess when the slide is in closed position. A protrusion separating both recesses must pass the helical spring respectively the bolt, when the slide should be displaced between its open position and its closed position. Overcoming the spring load is a tricky operation, because the slide is displaced at right angle to the direction in which the spring must be pushed back into the bore. Moreover, the slide can get caught in the spring and the spring may be damaged. The elastomeric synthetic bolt cannot be pushed back into the bore, since the synthetic material as a solid matter is not compressible. The slide must be twisted instead, to move it past the synthetic bolt. Consequently, the slide must be accordingly thin, to maintain within practical limits the force which must be applied upon displacement. With the small sizes which brackets have typically, the known bracket is difficult to realize.

A self-ligating bracket is disclosed in U.S. Pat. No. 5,613,850, in which the slide is combined with a U-shaped spring, which surrounds the slide. One or both branches of the spring is provided with a protrusion via an embossing process, so that it snaps in a recess of a bracket wing in closed position with its protrusion. Pressing down this branch enables to move the spring out of its snap-in position and to push the slide out of its closed position. The slide is not held in open position, so that it cannot be lost, which is uncomfortable in the mouth, because the slide could be swallowed.

A self-ligating bracket is disclosed in EP 1 679 048 A2, whose slide is maintained through a spring, which is inserted in a hole of the bracket body and engages in a continuous hole of the slide by means of a protruding, twice angled branch. The spring can be pushed out of the hole and the slide removed from the bracket. The spring is not able to hold the slide in open position. A further shortcoming is that food remains may build up in the hole of the slide and under the slide, which cannot be eliminated even by brushing one's teeth or repeated mouth washing.

A self-ligating bracket is moreover disclosed in EP 1 679 048 A2, whose slide has a long hole, through which a safety pin engages, which is anchored in a bore in the bracket, once the slide has been inserted in the bracket. The clearance exhibited by the safety pin in the long hole limits the path over which the slide can be displaced in the bracket between closed position and open position. Once the safety pin has been inserted the slide cannot be removed any longer. The safety pin is not able to hold the slide in closed position and in open position. Only friction can block the slide to a certain extent, which does not enable reliably to hold the slide in closed position or in open position.

Document DE 10 2006 053 215 A1 discloses a self-ligating bracket with a slide, which co-operates with a leaf spring arranged in the gingival wall of the bracket, which can be swung out sideways upon displacement of the slide. This bracket has the advantage that the leaf spring does not press against the underside of the slide and that the leaf spring can maintain the slide in its closed position as well as in its open position on the bracket body. If the bracket and its slide are however produced out of ceramic material by powder metallurgy, for example through a CIM process (Ceramic Injection Molding), it is then difficult to respect the strict dimensional tolerances required for such a bracket.

SUMMARY OF THE INVENTION

The object of the present invention is to provide a self-ligating bracket for orthodontics, in which the slot of the bracket can be closed by a slide, which even needs no particular elastic properties, can be formed mechanically stable, is maintained captive in closed position as well as in open position, is easy to open and to close, confers a pleasant aspect to the bracket and offers little opportunity for the build up of food remains which are difficult to remove. Moreover, the invention should be suitable for the production of ceramic brackets.

This object is met by a bracket having the features specified in the claims.

The bracket according to the invention consists of means that can hold the slide in its closed position as well as in its open position, an elongated recess, which is provided in the gingival wall and/or in the occlusal wall of the bracket and has an opening facing the slide, out of which a strand protrudes to the outside with a section of the lateral surface thereof, which strand rests in the recess and is supported in the recess. The strand is deformable either elastically or elastomerically or it is supported elastically or elastomerically. This enables the strand to be resilient, for instance, to yield, when the slide abuts against the section of the strand which protrudes from the opening of the recess, when said slide is displaced with a protrusion or stop provided on its underside. By underside of the slide is meant the side of the slide facing the base of the bracket. A first stop provided on the slide abuts the strand when the slide is in open position, which prevents the slide from slipping out of its guide completely; the slide remains far more in its open position with the bracket connected in a captive relationship.

The protrusion provided on the underside of the slide is arranged in such a way that upon displacement of the slide into the closed position thereof, before assuming the closed position, it abuts the strand. When displacing the slide further to the closed position thereof, this protrusion can overcome the section of the strand protruding from the recess, inasmuch as the strand evades the protrusion against an elastic or elastomeric reset force, for example as the protrusion deforms the strand. The same goes upon displacement of the slide into its open position. The yielding or the deformation of the strand reduces the amount with which it protrudes from the recess. This enables the protrusion on the underside of the slide to overcome the strand more precisely with a certain resistance, without however subjecting the slide to torsion.

When the slide, upon displacement in the closed position thereof, has overcome the strand with its protrusion, said slide should recover resiliently its original position or form. This enables providing there is sufficient space on both sides, i.e. relative to the displacement direction of the slide on the front as well as on the back of the protrusion, to accommodate the section of the strand protruding from the recess, preferably so that no more reset force is present in the contained section of the strand respectively no more reset force acts upon the strand. The room, in which the protruding section of the strand rests, when the slide is in the closed position thereof, need not be larger or not substantially larger than the protruding section of the strand, so that said section secures the position of the slide in the closed position thereof, free from backlash or with little play. The room, in which the protruding section of the strand is situated, when the slide is in the closed position thereof, can also be larger than the extension of the strand in moving direction of the slide, when said slide in the closed position thereof abuts a second stop, which is provided on the bracket body.

The invention has significant advantages:

- A strand, which due to its construction type and its lying flat position, can be deformed and/or pushed back by the slide upon the displacement thereof, enables to pass the strand only by exerting a set force which is determined by the generated reset force of the strand, which acts in the strand or upon the strand.
- When shifting the slide from the open position into the closed position, a resilience or an elastomeric reset force must now be overcome, when the protrusion provided on the underside of the slide abuts the strand and then overcomes it by deforming or pushing it back. As long as the strand is neither deformed nor pushed back, no reset force need be overcome, because the strand need not lean on the underside of the slide with a given pressure. The strand may still lie flat on the lower side of the slide. The force hence exerted upon the slide is preferably minimal; it is any way substantially smaller than the force to be exerted when overcoming the protrusion.
- The slide can be displaced until the protrusion of the slide abuts the strand, easily and without particular force. The force required increases only shortly before reaching the closed position and the snap-in process becomes noticeable, which indicates that the slide is secured in the closed position thereof.
- When the slide is inserted in its guide for the first time, the strand can be passed by deformation or displacement and the slide then switches into its open position, in which it is prevented from slipping out of the guide again, thanks to the first stop which is provided on the underside of the slide and passes the strand when the slide is placed in its guide for the first time.
- Since it needs be exposed to torsion upon displacement between the open position and the closed position, the slide can be rigid by design. It favours the production of the bracket and of its slide of ceramic and is quite suitable to absorb forces which are exerted by an archwire situated in the slot of the bracket on the underside of the slide.
- There is no need to provide a reach-through opening, which is difficult to clean, either in the bracket or in its slide.
- A depression can be provided for instance in the upper side of the slide, which is easy to clean, for activating the slide. The treating orthodontist can reach into the depression for pushing the slide with a tool. Incidentally, the upper side of the slide can be smooth by design and be flush-mounted with the upper side of the adjoining ligature wing, which is not only suitable for cleaning but also conveys the bracket an appealing external appearance, without compromising the technical function of the bracket.
- The invention lends it for use with brackets, which may consist of any materials known for brackets, namely for brackets and slides made of metal, of ceramic and/or of synthetic material, whereas ceramic is preferred.

The strand can be hollow by design; but it is preferably not hollow, in order to prevent deposits, such as plaque for example, which cannot be removed.

The strand can even consist of an elastic or elastomeric material and then is supported ideally on an unyielding abutment, which is provided opposite to the underside of the slide in the recess in the bracket body and preferably forms the end surface thereof.

It is particularly advantageously that the strand is unyielding by design and is supported by an elastically or elastomerically yielding abutment, with its side facing away from the slide in the recess. It has significant advantages:

- There can be a longer pitch of spring than in the opposite case i.e. with an unyielding supported elastic or elastomeric strand.
- The friction is lower upon displacement of the slide than in the opposite case.
- The abrasion is lower upon displacement of the slide than in the opposite case.
- The snap-in of the slide into the closed position can be better heard than in the opposite case.

As regards the size of forces typically generated upon displacement of the slide of the self-ligating orthodontic bracket, it should be decided whether a strand or the abutment supporting it in the sense of the invention is designed elastically or elastomerically yielding or unyielding.

In every case, the strand is preferably rectilinear, in particular cylindrical.

Preferably, the strand protrudes at most with its semi-periphery from the opening of the recess in the bracket body. This enables to guarantee that the strand is not pulled out of the recess upon displacement of the slide. If the strand is cylindrical the circumferential section of the strand protruding over the opening of the recess tapers as it moves away from the opening of the recess and makes it easier to move the protrusion provided on the underside of the slide past the strand. Such an operation is moreover facilitated in that the strand, as long as it is not deformed by the displacement of the slide, does not touch both longitudinal walls of the recess as of the rim of the opening of the recess, but only at a distance from the rim of the recess when—as preferred—the strand protrudes over the rim of the opening of the recess with less than half its circumference. The deformation and displacement of the strand is facilitated when the slide abuts the strand with its protrusion provided on the underside of the slide.

This advantage is not only provided with a cylindrical strand, but also with a strand, which protrudes over the rim of the opening of the recess with a wedge-shaped section, especially when the wedge-shaped section extends over a short length into the recess. The section situated completely in the recess, adjoining the wedge-shaped section, rests against both side walls of the recess and against the bottom of the recess preferably over its whole surface. The bottom of the recess forms for the strand an abutment which supports the strand. The abutment can be unyielding if a flexible material is used for the strand. If an unyielding material is used for the strand, the abutment should be able to yield.

The strand has in the recess, in which it lies, preferably no lateral play, to provide a firm support thereto and to prevent the deposit of plaque in the recess as much as possible. The requirement that the strand preferably should not have any lateral play in its recess does not mean that its tapering section may not be remote from the side walls of the recess.

The length of the recess, in which the strand rests, is preferably smaller than the width of the slide, so that the slide can completely span the recess and the strand situated therein. This prevents the build up of deposits in the recess. The length of the strand and the length of its recess should match preferably.

The strand should preferably be inserted in the first wall of the bracket. By the first wall of the bracket is meant the wall on which the slide is introduced in its guide. The second stop against which the slide abuts in the closed position thereof, is preferably formed on the opposite second wall of the bracket and preferably arranged in such a way that the slide abuts with the front end thereof against the second stop. By front end of the slide is meant the end which is situated at the front when the slide is displaced.

The strand is preferably provided in the gingival wall of the bracket, whereas the second stop is provided on the occlusal wall, so that the slide, when the bracket is glued to a tooth, is transferred, starting from the gingiva, from its open position to its closed position. The strand can also perfectly be provided in the occlusal wall, whereas the second stop is provided on the gingival wall in such a case, so that the slide is transferred into the closed position thereof from the occlusal side in the gingival direction. This variation offers particularly high safety as it prevents the slide from being pressed open when biting the teeth together.

The bracket according to the invention comes with a single strand in the gingival or occlusal wall of the bracket, which is arranged preferably centrally with relation to the length of the bracket. The length of the bracket is measured in longitudinal direction of the slot.

A bracket, in which a strand is arranged in the gingival wall as well as in the occlusal wall of the bracket, is more expensive, but still possible. In such a case, a strand, preferably the strand in the gingival wall, enables to prevent the slide from getting lost, when it is in open position, whereas conversely the other strand, preferably the strand in the occlusal wall, enables to secure the slide in the closed position thereof. Both strands rest in their own recesses, which extend parallel to the groove, which the slide bridges in the closed position thereof.

In the embodiment of the bracket with two strands i.e. one strand on each side of the slot, only a single stop should be arranged on the underside of the slide, against which the second strand can abut in the closed position of the slide. Starting from this stop, the displacement region of the slide between its closed position and its open position requires a flat, preferably cuboidal recess, in which the protruding circumferential sections of both strands may engage and which extends in the displacement direction at least over such a length that in closed position of the slide, both strands may engage into a flat recess on the underside of the slide. The length of the flat recess measured in the displacement direction on the underside of the slide is hence at least equal to the distance of both strands, measured over the sides of their protruding ends facing away from one another.

This variation of the invention enables to dispense with a protrusion situated therebetween on the underside of the slide.

Preferably, the construction of the bracket is such that only a single strand is provided in the gingival wall and/or in the occlusal wall, which is preferably designed cylindrical.

The opening of the recess accommodating the strand extends from the base of the bracket and the recess is more appropriately oriented in such a way that it runs vertically or approximately vertically with respect to the slide in the gingival wall respectively in the occlusal wall of the bracket.

The slide is preferably a mainly flat structure, which is received in straight guides. But it is also possible to provide guides which run along an arc of a circle and to introduce an accordingly curved slide in such guides.

The strand can be fixed in the recess receiving it, for instance by gluing. But the strand can also be laid in its respective recess, without fixing it by an adhesive, since it is secured by said slide at least in closed position of the slide, preferably also when the slide is in open position.

When a flexible strand is used it then consists preferably of a synthetic material with elastic or elastomeric restoring capacity, in particular of polyoxymethylene (POM), of a polyetherketone (PEK) or of a polyetheretherketone (PEEK), which combine sufficient strength with sufficient restoring capacity and with sufficient durability under the conditions prevailing in the mouth and are sufficiently biocompatible.

The bracket and its slide consist preferably of a ceramic, the bracket preferably made of aluminium oxide, the slide preferably made of a ceramic with greater strength than aluminium oxide, in particular made of zirconium oxide. That is particularly advantageously, when using a flexible strand, in particular in combination with a strand made of POM, PEK or PEEK, because they do not compromise the general aesthetic impression of a ceramic bracket because of their light colour, contrary to a metallic spring or to a dark elastomeric strand, which would show through a thin ceramic slide with a detrimental effect. The colour of the teeth can however show through the ceramic without detrimental effect. The invention moreover enables with the incorporation of a synthetic strand to compensate for the manufacturing tolerances of the bracket and of its slide.

When using an unyielding strand, it consists preferably of a ceramic, in particular of the same ceramic as the slide. A ceramic strand proves particularly inconspicuous in the appearance of the bracket and can mask the abutment consisting of another material.

The result is particularly impressive with a further embodiment of the invention as regards a tolerance compensation if the recess is formed by a slit, which extends from the opening facing the slide continuously up to the underside of the base of the bracket and when a plug is inserted in the slit, on which the strand is supported. After laying in the strand in its recess, inserting the slide in its guide and pushing the slide forward into its closed position, the plug can be pushed forward in the direction towards the slide, until the strand arranged between the plug and the slide touches the underside of the slide, which enables to terminate the advance movement of the plug. This advance movement of the plug can be performed with such little force that the yielding strand, when used for attachment to the underside of the slide, is at best negligibly compressed. Any residual compression can for instance be avoided inasmuch as the elastic respectively elastomeric strand and the plug are left first of all to the free play of the forces, once the advance movement of the plug has come to an end so that possible compression of the strand may reappear due to the restoring capacity thereof. The position of the plug can then be fixed in the slit, for instance by filling the free space between the specific end of the plug, which faces away from the slide, and the underside of the base of the bracket with a hardening adhesive. It can then be for instance an adhesive as used usually for gluing brackets on teeth.

If instead of the strand the plug is yielding one can proceed accordingly advantageously and push the strand forward using the plug against the underside of the slide, without compressing the plug.

In this manner, it can be guaranteed in both cases that independently of dimensional tolerances, which have an influence on the cooperation between the bracket and its slide, the strand which co-operates with the slide, which can co-operate in this function, that is to say with the slide, remains substantially uninfluenced by the dimensional tolerances.

The plug preferably fills up the whole cross-section of the slit, so as not to offer any free space for deposits as far as possible. When using a yielding strand, the plug may consist of ceramic, but preferably of synthetic material, in particular of an unyielding synthetic material. When using an unyielding strand, the plug consists suitably of an elastomeric synthetic material.

The plug, which supports the strand, has preferably grooves, which run in the direction from the base to the slide, i.e. in lingual-labial direction. An adhesive can penetrate into these grooves, whereas the plug is fixed in the recess of the bracket body with said adhesive. The anchoring of the plug is hence enhanced.

Preferably, the plug is stepped in such a way that it only partially fills up the cross-section of the recess in close vicinity of the strand and thus creates a space into which the strand can be pushed back by elastic or (preferably) by elastomeric deformation.

BRIEF DESCRIPTION OF THE DRAWINGS

Further features and advantages of the invention are described below using exemplary embodiments which are illustrated in the appended drawings. Identical and correlating parts are designated with matching reference numbers in the examples of embodiment.

FIG. 1 shows a first bracket in a view on the gingival side of a bracket with a slide in open position, FIG. 2 shows the side view II of the bracket, FIG. 3 shows the section A-A of the closed bracket, FIG. 3a shows an enlarged detail "J" of FIG. 3.

DETAILED DESCRIPTION

Figure 4:
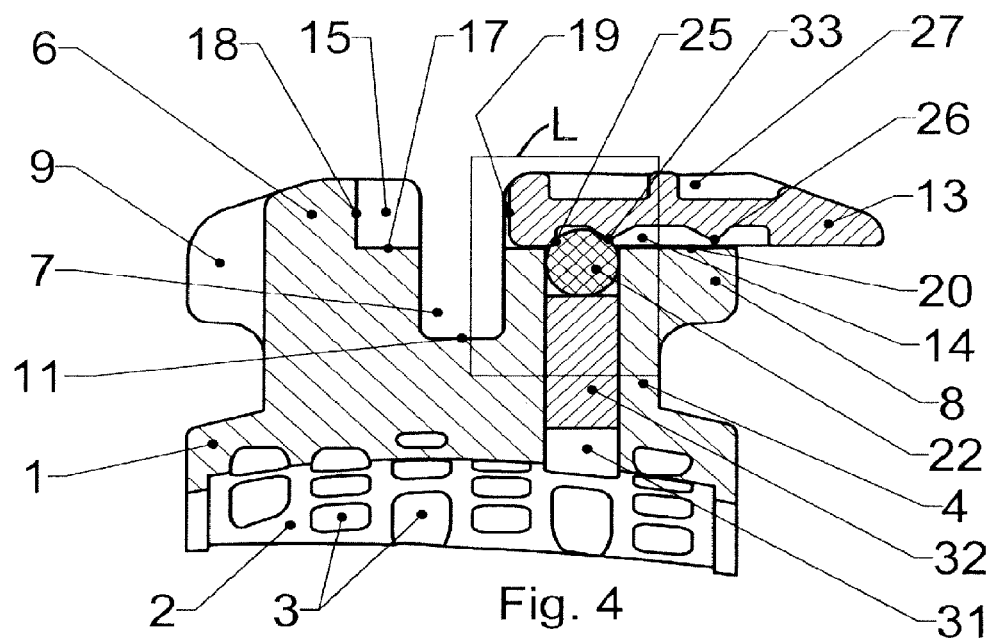
FIG. 4 shows a section as in FIG. 3, however with the slide in its open position.
Figure 4A:
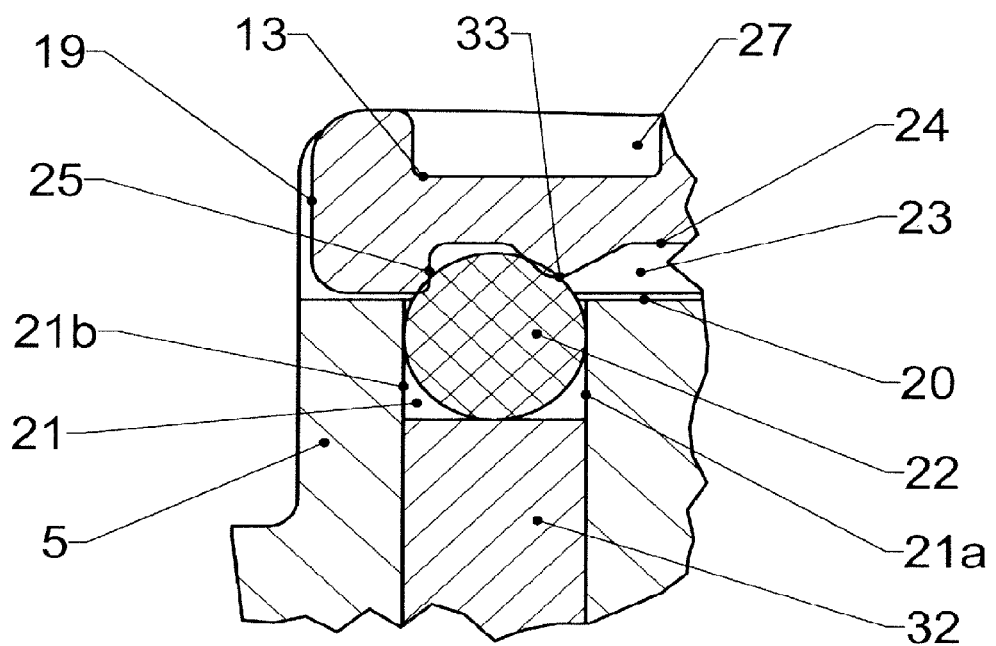
FIG. 4a shows an enlarged detail "L" of FIG. 4.

The bracket illustrated in the figures has a cambered base 1, whose camber is approximately adapted to the front side of a tooth. The base 1 has in its underside 2, which forms the lingual side of the bracket, depressions 3 arranged successively, which are undercut. In the section, as represented on FIG. 3, the depressions 3 have a rectangular contour. In a section positioned vertically thereto, the depressions 3 have, as represented on FIG. 7 or FIG. 8, a rhombic contour. An adhesive can be coated on the underside 2, to glue the bracket on a tooth. The interlocking of the undercut depressions 3 with the adhesive enables to obtain good adherence. In every single row, the depressions 3 and the undercuts are oriented in a matching manner. From row to row, they are however oriented alternately in one direction and in the other direction. This enables to obtain the same adherence with a thrust acting on the bracket in the direction from mesial to distal such as in the case of a thrust from distal to mesial whereas in the case of a thrust in the direction occlusal-gingival or gingival-occlusal, the adherence is highly independent of the direction of thrust.

The base 1 turns into a socket 4 receiving a gingival wall 5 and a occlusal wall 6. Both walls 5 and 6 run parallel relative to one another and are separated by a slot 7, which runs continuously rectilinear from distal to mesial and is open to labial.

A ligature wing 8 protruding in the gingival direction is provided on the gingival wall 5. A ligature wing 9 protruding in the occlusal direction is provided on the occlusal wall 6. Ligature wires can be installed thereon in a way known to the man of the art. The ligature wings 8 and 9 may alternately be subdivided in a pair of ligature wings.

The slot 7 is used for receiving an archwire 10, which has in particular a rectangular cross-section, is not integral part of the bracket and therefore only represented in dotted lines with its contour on FIG. 2. Pressure can be exerted on the bottom 11 of the slot and a torque can be exerted on the walls 5 and 6 of the bracket through tightening of the archwire 10. For that purpose, the clear cross-section of the slot 7 is substantially rectangular. In the present case, said cross-section is limited by the bottom 11 of the slot 7 as well as by the gingival wall 5 and by the occlusal wall 6. The edges 12 at the ends of the slot 7 are rounded. Moreover, at least the edges of a slide 13 which delineate the slot 7 upwards are also rounded. This serves for reducing the friction for the archwire 10 situated in the slot 7 and proves particularly advantageous in case of major malpositions of the teeth, which require the path of the archwire 10 to be particularly irregular.

A labial recess 14 in the gingival wall 5 and a labial recess 15 in the occlusal wall 6 receive the mainly flat slide 13 with rectangular contour. The recesses 14 and 15 have undercuts 16 which are parallel relative to one another and to the bottom 11 of the slot 7, which together with the bottom 17 of the recess 15 and the bottom 20 of the recess 14, form a slide guide for the slide 13, which the slide 13 cannot leave in labial direction, because the undercuts 16 prevent it. The recesses 14 and 15 lie in a common alignment. The recess 14 runs through the gingival wall 5, while the recess 15 ends against a stop 18 in the occlusal wall 6, i.e. the "second" stop mentioned in the patent claims.

Figure 5:
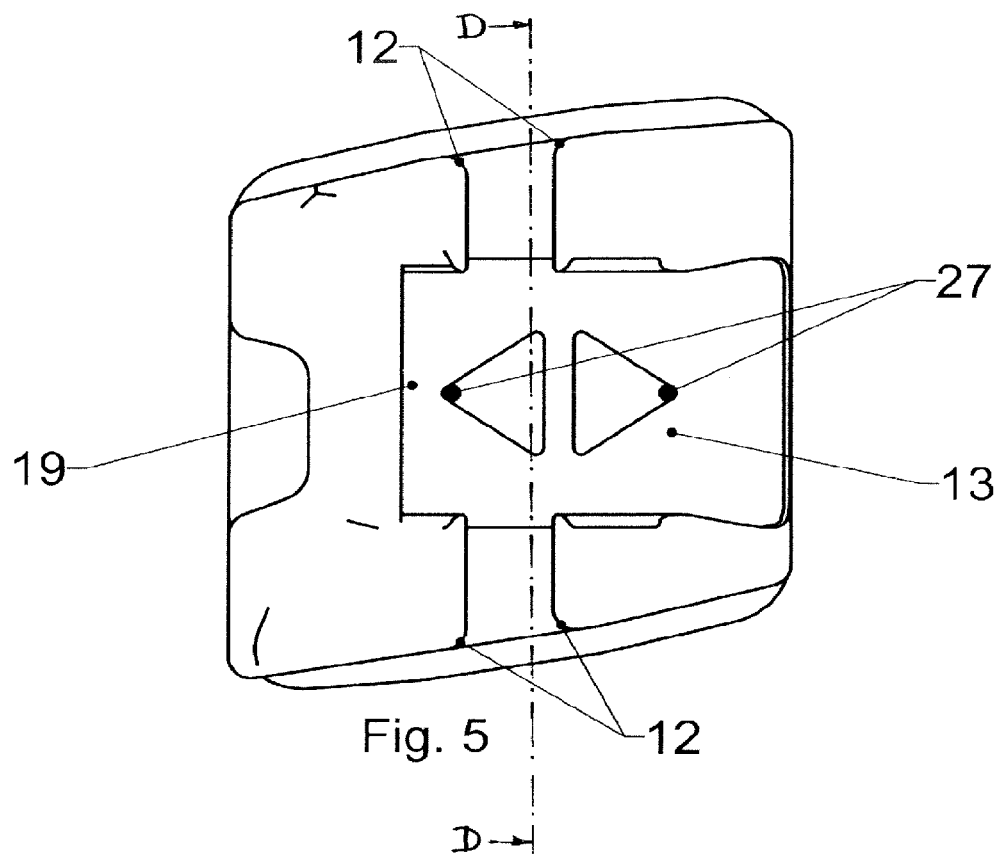
FIG. 5 shows the bracket in elevation view.
Figure 6:
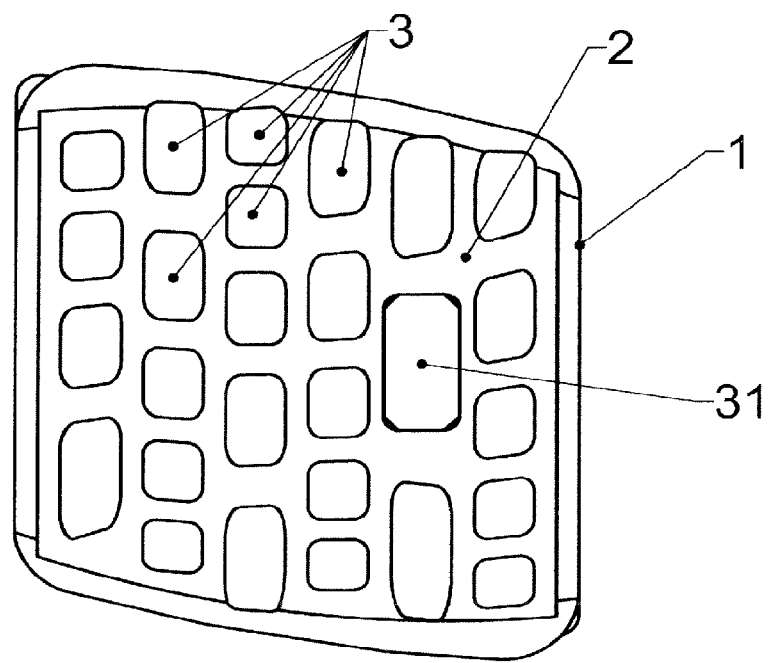
FIG. 6 shows the bracket in a view from below.
Figure 7:
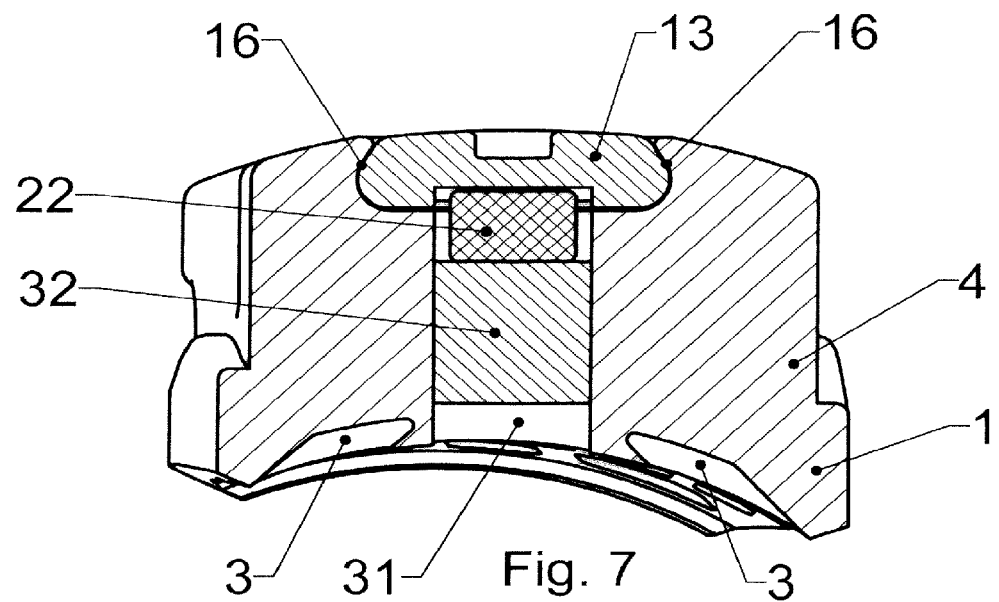
FIG. 7 shows the section C-C of the bracket.
Figure 8:
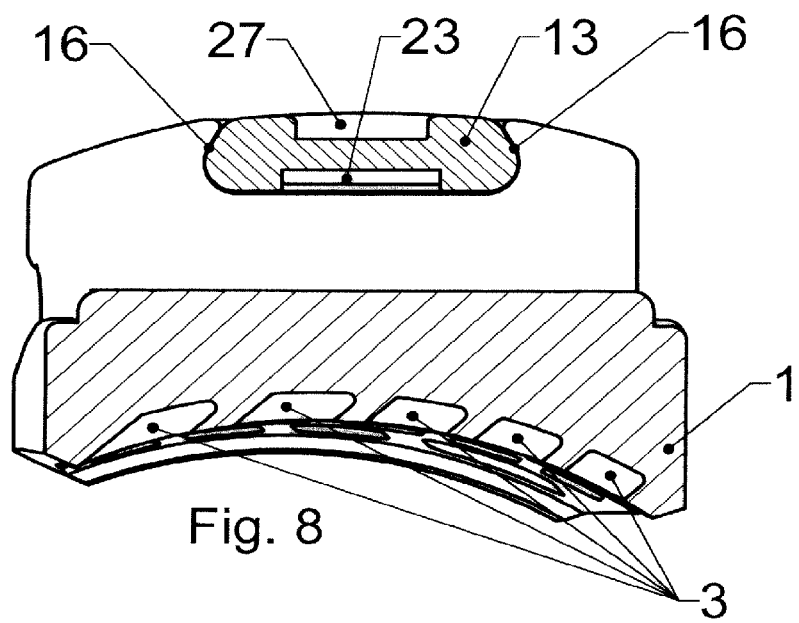
FIG. 8 shows the section D-D of the bracket.

The slide 13 can be displaced in the guide 15 to 17 in the gingival-occlusal direction between an open position, which is represented on FIG. 4, and a closed position, which is illustrated in FIGS. 2, 3 and 5. In open position, the slot 7 is open over its whole width from the labial side. The front end 19 of the slide 13 closes preferably with the surface of the gingival wall 5 delineating the slot 7, as illustrated in FIGS. 2 and 7. In closed position, the front end 19 of the slide 13 strikes against the second stop 18 on the occlusal wall 6, such as it is illustrated particularly clearly on FIG. 3. In closed position, the slide 13 bridges the slot 7, so that an archwire 10 running therein cannot leave the slot 7 in labial direction.

The gingival wall 5 includes a slit-shaped recess 21, which extends mainly in parallel to the surface of the wall 5 delineating the slot 7. The surfaces 21a and 21b extending in direction of the slot 7, opposite to one another, run parallel relative to one another, so that the slit-shaped recess 21 has a cuboidal form.

The slit-shaped recess 21 is a section of the slit 31 of rectangular section, which runs through from the labial upper side of the bracket body under the slide 13 up to the underside 2 of the base 1. A plug 32 is inserted in this slit 31 and supports a cylindrical strand 22 which preferably consists of an elastomeric synthetic material. The position of the plug 32 is selected in such a way that the strand 22 supported by the plug 32 abuts against the underside of the slide 13 when said slide is in closed position, preferably without exerting a significant pressure on the underside of the slide. The plug 32 is fixed in this position, preferably using an adhesive The strand 22 protrudes over the labial rim of the recess 21 with less than half its circumference and engages into a recess 23, which is provided on the underside of the slide 13. The recess 23 has a rectangular contour. Said recess forms a stop 25, which abuts against the lateral surface of the strand 22 which projects over the labial rim of the recess 21, when the slide 13 is in its open position, see FIGS. 3 and 3a. In the stop 25, it is the "first" stop specified in the patent claims. It thus prevents the slide 13 from slipping down from the bracket unintentionally when it is in open position.

In order to secure an archwire 10 situated in the slot 7, the slide 13 is transferred into its closed position illustrated on FIG. 3, in which the front end 19 of the slide 13 abuts the stop 18 on the occlusal wall 6. In order to be able to hold the slide 13 in the closed position thereof, a protrusion 26 is provided in the recess 23 on the underside of the slide 13, which is wedge-shaped with the illustrated exemplary embodiment, at an angle of more than 90° between both its wedge surfaces, but can also have the form of a circular segment in its cross-section for instance. The protrusion 26 extends parallel to the slot 7 and to the strand 22. Its height above the bottom 24 of the recess 23 is smaller than the depth of the recess 23.

The protrusion 26 is arranged in such a way that when said slide 13 is in closed position it rests on the side of the strand 22 pointing to the slot 7 and touches the strand 22, see FIG. 3a. The position of the protrusion 26 is preferably selected in such a way that the strand 22 when said slide 13 is in closed position has substantially reduced its reset force, so that the strand 22 is substantially inert. When shifting the slide 13 into its closed position, the protrusion 26 can overcome the section of the strand 22 which projects over the labial rim of the recess 21. As soon as the apex of the protrusion 26 has passed the strand 22, said strand recovers its substantially cylindrical form under the effect of the reset force which had built up previously. For shifting the slide 13 into its open position, greater resistance must be overcome than when closing since the strand 22 in such a case must be passed by a steeper wedge surface of the protrusion 26 than when closing the bracket. The resistance, which must be overcome when opening the bracket, is sufficient to hold the slide in the closed position thereof in spite of the forces typically generated in the mouth. To be able to produce the force to open the bracket, at least one depression 27 is provided in the upper side of the slide 13, into which depression one can engage with a tool, for example with a scaler, for shifting the slide 13.

A second protrusion 33 is provided in the recess on the underside of the slide 13, to hold the slide 13 in its open position. The operating mode of the protrusion 33 corresponds to that of the protrusion 26. The protrusion 26 is preferably greater than the protrusion 33, because it is more important to secure the closed position than the open position. The protrusion 33 is not absolutely necessary since the slide can be maintained in open position under certain circumstances also using various friction forces.

Figure 9:
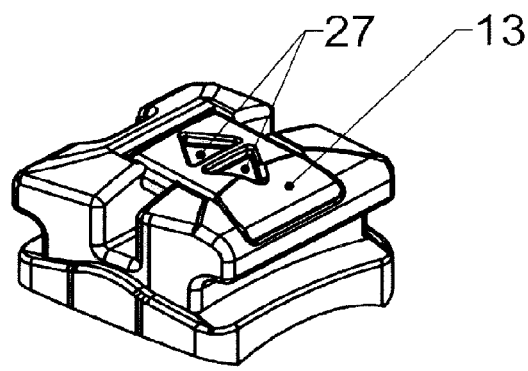
FIG. 9 shows an isometric view of the bracket in its closed position.
Figure 10:
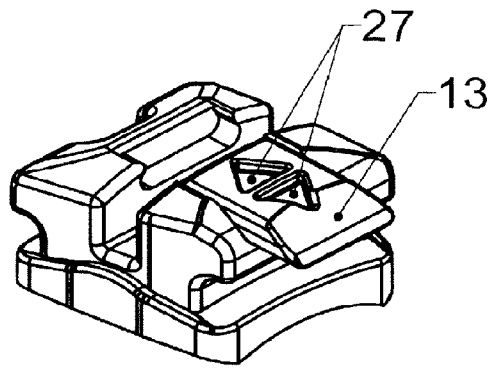
FIG. 10 shows the bracket illustrated in FIG. 9 with the slide in its open position.

The bracket is represented in isometric views in FIGS. 9 and 10, which clearly show that the depressions 27 taper in displacement direction, i.e. are triangular. A tool can be engaged into these depressions 27 for opening or closing the slide 13. Since the respective depressions 27 taper in the displacement direction intended for opening as well as closing, it is easier to operate the slide 13 in this manner.

Figure 11:
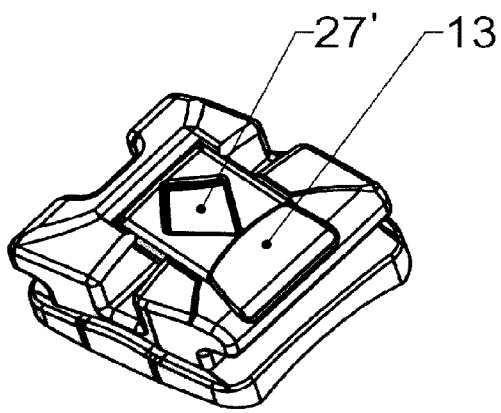
FIG. 11 shows an isometric view of a second bracket, whose slide presents a rhombic depression and is in its closed position.
Figure 12:
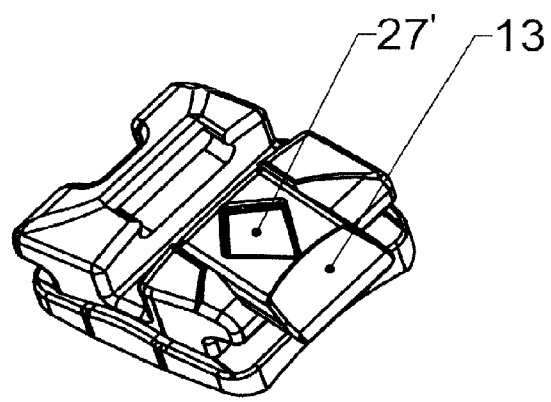
FIG. 12 shows the bracket illustrated in FIG. 11 with the slide in its open position.
Figure 13:
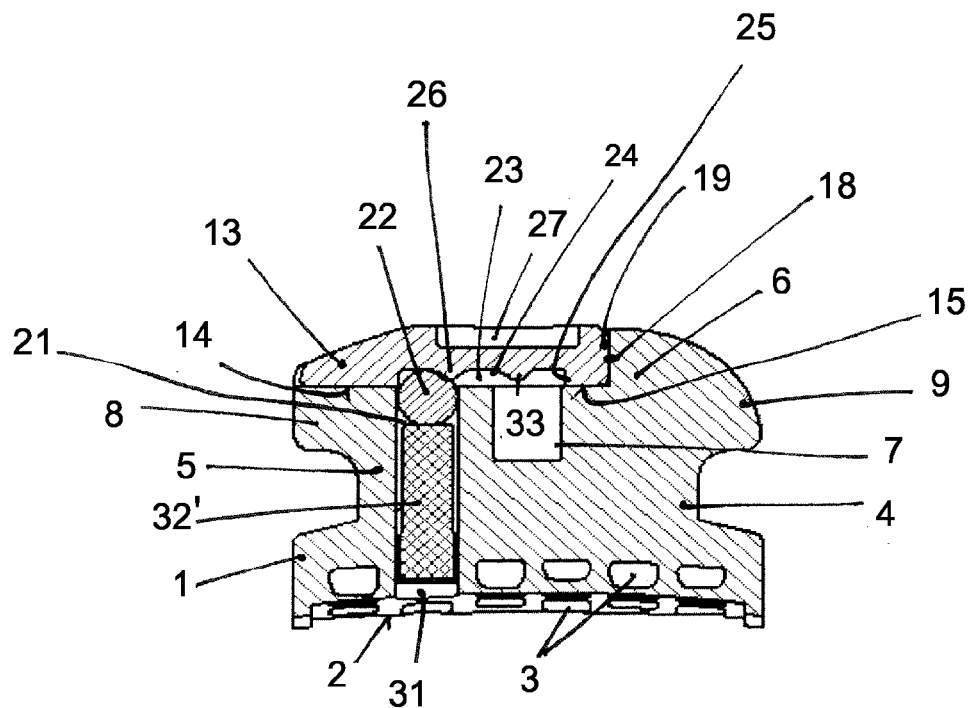
FIG. 13 shows a third bracket in a section corresponding to FIG. 3, along the section plane A-A on FIG. 15, with a slide in closed position.
Figure 14:
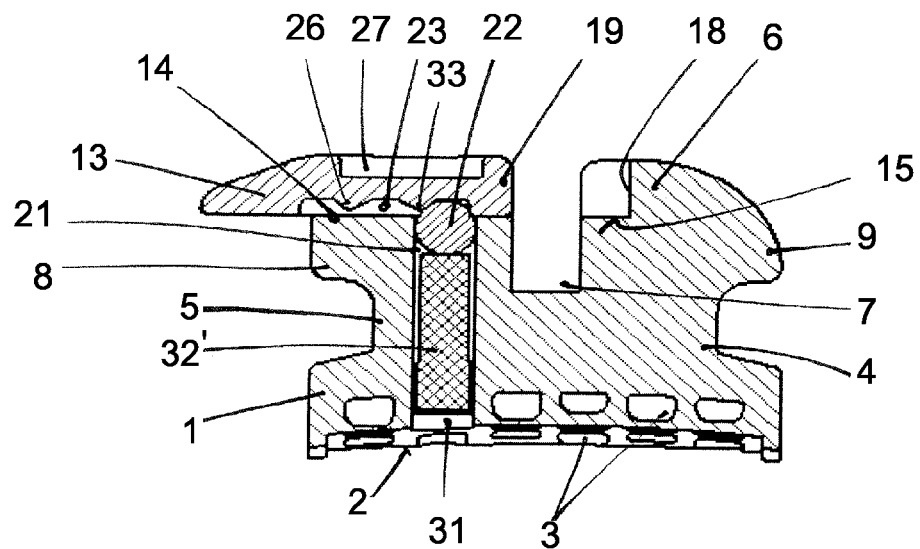
FIG. 14 shows a section through the third bracket as in FIG. 13, however with the slide in open position.
Figure 15:
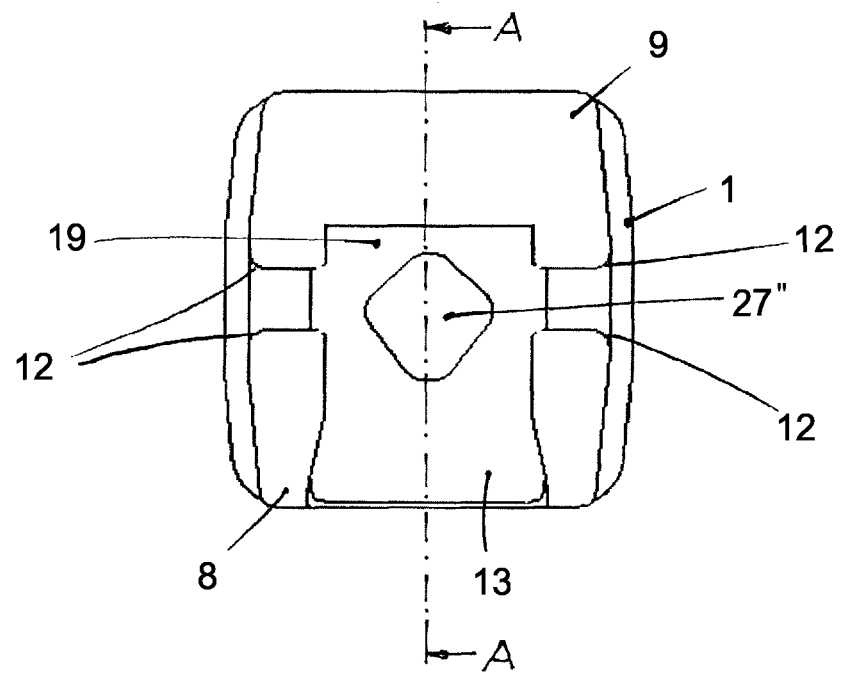
FIG. 15 shows the third bracket in an elevation view on its labial side.
Figure 16:
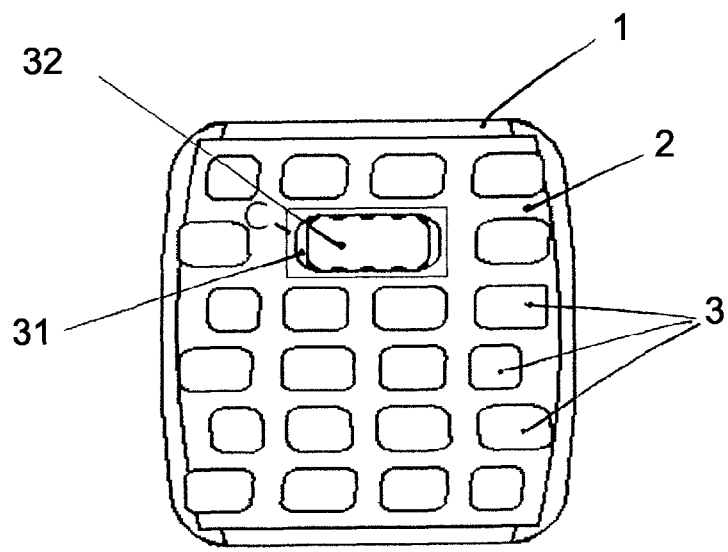
FIG. 16 shows the third bracket in an elevation view on its lingual side.
Figure 17:
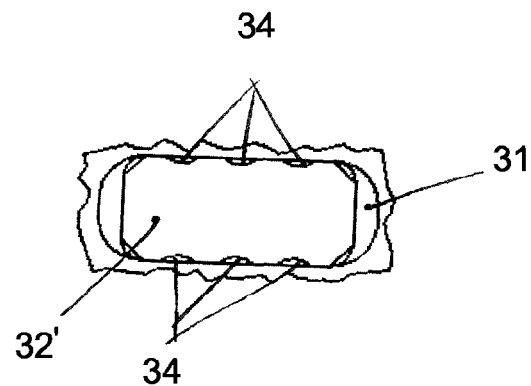
FIG. 17 shows the detail C of FIG. 16 in enlarged scale.
Figure 18:
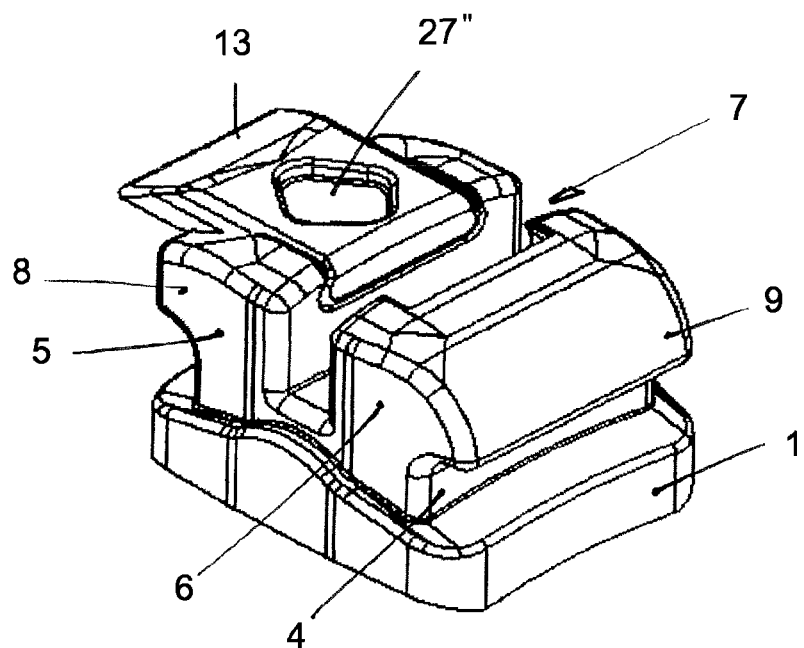
FIG. 18 shows the third bracket in an oblique view with the slide in its open position.
Figure 19:
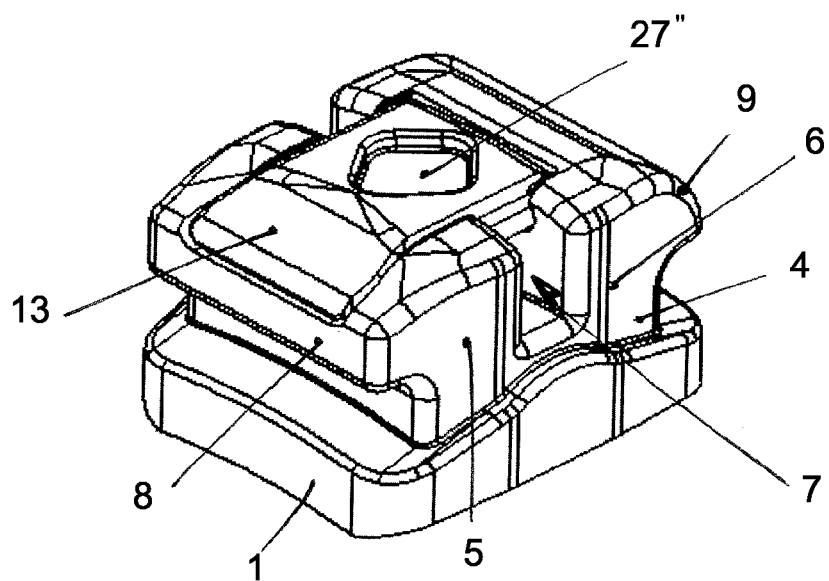
FIG. 19 shows the third bracket in an oblique view with the slide in its closed position.
Figure 22:
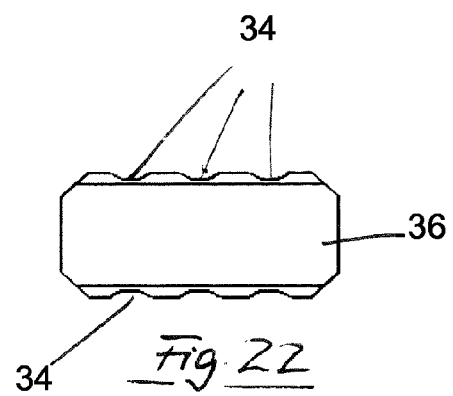
FIG. 22 shows the plug of FIG. 20 in an elevation view on its labial side.
Figure 21:
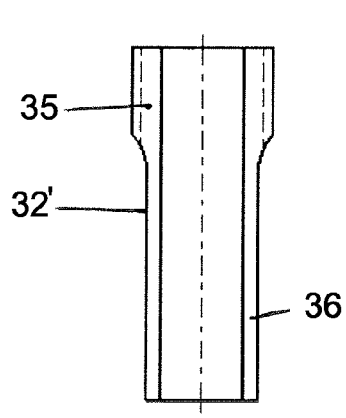
FIG. 21 shows the plug of FIG. 20 in an elevation view on one of both its narrow sides.
Figure 20:
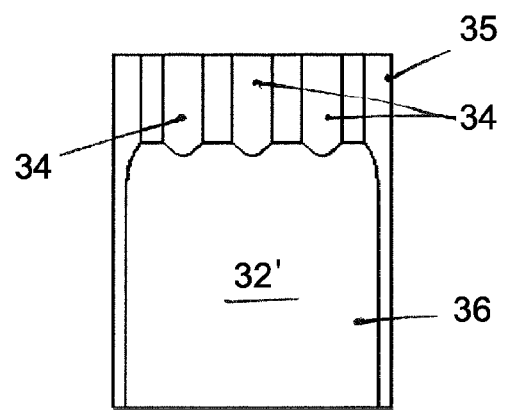
FIG. 20 shows in detail the plug provided in the third bracket in enlarged scale in an elevation view on one of both its wide sides.
Figure 23:
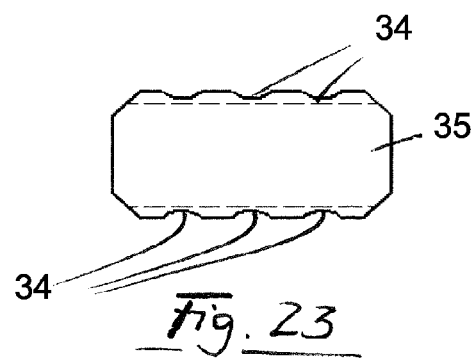
FIG. 23 shows the plug of FIG. 20 in an elevation view on its lingual side.
Figure 24:
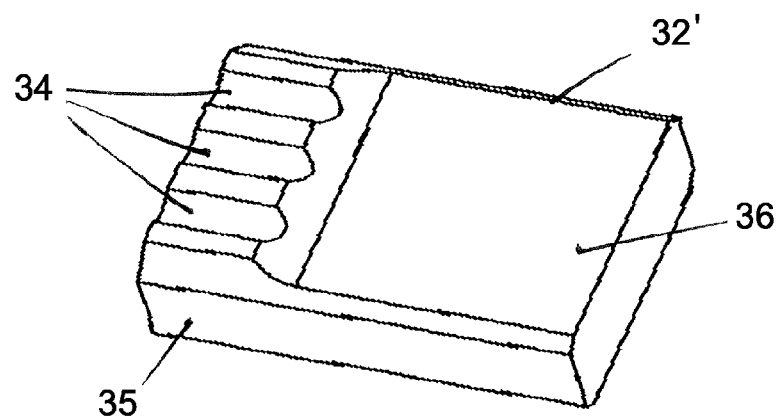
FIGS. 24 and 25 show the plug of FIG. 20 in two different oblique views.
Figure 25:
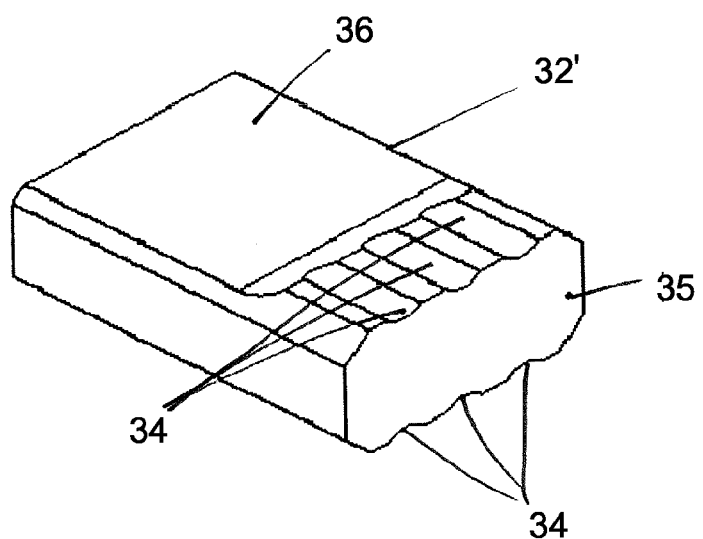

Both depressions 27 can be grouped into a single depression 27', as is illustrated in FIGS. 11 and 12. The depression 27' of the exemplary embodiment illustrated in FIGS. 11 and 12 also tapers in longitudinal direction of the slide 13 up to the ends thereof, hence tapers in the corresponding displacement direction and thus facilitates the operation of the slide 13 with an appropriate tool.

The bracket illustrated in FIGS. 13 to 20 bears a strong resemblance with the brackets illustrated in FIGS. 1 to 12. The views illustrated in FIGS. 1 and 2, except for small deviations, insignificant for the present invention, for the third bracket illustrated in FIGS. 13 to 20.

The third bracket differentiates from the first bracket illustrated in FIGS. 1 to 10 substantially in that the cylindrical strand 22 does not consist of an elastomeric synthetic material, but of a ceramic material and that the plug 32', which supports the cylindrical strand 22, does not consist of a ceramic material or similar unyielding material, but of an elastomeric synthetic material. If upon displacement of the slide 13 between its open position (FIG. 14) and its closed position (FIG. 13), the protrusions 26 and 33, which are designed on the underside of the slide 13, hit the strand 22, the strand 22 can only therefore be resilient and retract into the slit 31, because the forces exerted by the protrusions 26 and 23 upon the strand are transmitted to the plug 32' and said strand can yield due to its elastomeric behavior, inasmuch as it is deformed by compression. This enables the cross-section of the plug 32' to have a smaller section immediately adjoining the strand 22 than the clear cross-section of the slit 31, which runs from the underside 2 of the base of the bracket through to the bottom 20 of the recess 14 provided in the bracket body, in which recess the slide 13 is installed.

The plug 32' is fixed in the slit 31 by gluing. The adhesive can be poured for that purpose from the underside 2 of the bracket into the slit 31. The lower end of the plug 32' is provided at a distance from the underside 2 of the bracket, which enables to form a free space under the plug 32', which can absorb the adhesive.

As can be seen on FIGS. 20 to 25, the plug 32' has a socket 35, which exhibits grooves 34 on both its wide sides, which extend in lingual-labial direction. The socket 35 is inserted free from backlash in the slit 31, see FIG. 17. A portion of the adhesive, which is poured from the underside 2 of the bracket into the slit 31, penetrates into the grooves 34 and improves the adherence of the plug 32' in the slit 31. A narrower section of the plug 32' is adjoining the socket, which is remote from the walls of the slit 31, which enables to provide a free space, in which the narrower section 36 can be deformed reversibly during the compression of the plug 32'.

For being activated, the slide 13 has a rhombic depression 27" on its labial upper side, similar to the rhombic depression 27" in the second exemplary embodiment according to FIGS. 11 and 12.

| Reference numbers | |
|---|---|
| 1 | Base |
| 2 | Underside |
| 3 | Depressions |
| 4 | Socket |
| 5 | Gingival wall |
| 6 | Occlusal wall |
| 7 | Slot |
| 8 | Gingival ligature wing |
| 9 | Occlusal ligature wing |
| 10 | Archwire |
| 11 | Bottom of 7 |
| 12 | Edges of 7 |
| 13 | Slide |
| 14 | Labial recess in 5 |
| 15 | Labial recess in 6 |
| 16 | Undercuts |
| 17 | Bottom of 15 |
| 18 | Second stop |
| 19 | Front end of 13 |
| 20 | Bottom of 14 |
| 21 | (slit-shaped) recess in 5 |
| 21b | Surface of 21 |
| 21b | Surface of 21 |
| 22 | Strand |
| 23 | Recess in the underside of 13 |
| 24 | Bottom of 23 |
| 25 | Stop, first stop |
| 26 | Protrusion on 24 |
| 27 | Depression |
| 31 | Slit |
| 32 | Plug |
| 33 | Protrusion |
| 34 | Grooves in 32 |
| 35 | Socket of 32 |
| 36 | Narrower section of 32 |

The invention claimed is:

1. A self-ligating bracket for orthodontics comprising:
a base,
an occlusal wall extending from the base and having at least one occlusal ligature wing,
a gingival wall extending from the base and having at least one gingival ligature wing,
a slot, which separates the occlusal wall and the gingival wall from one another and extends continuously in a direction from mesial to distal,
a slide, which is held in a guide provided in the occlusal wall and/or in the gingival wall, and in the guide can be shifted in a gingival-occlusal direction between a closed position, in which the slide bridges the slot, and an open position, in which the slot is open in a labial direction,
an elongated recess provided in the gingival wall or in the occlusal wall of the bracket and having an opening facing the slide, wherein a longitudinal direction of the elongated recess runs parallel to a longitudinal direction of the slot,
and a structure, that can hold the slide in the closed position as well as in the open position,
wherein:
the structure that can hold the slide comprises a strand, wherein the strand is elastically and elastomerically unyielding, the strand having a cylindrical lateral surface wherein the strand is arranged horizontally in the recess, the strand having a part of the lateral surface facing towards the slide and another part of the lateral surface facing towards the base, is supported in the recess and rests on an elastically or elastomerically yielding plug with the part of the lateral surface facing towards the base and can give way to a movement of the slide because the plug can be elastically or elastomerically deformed by the moving slide;
a first stop is provided on the slide, which abuts the lateral surface of the strand in the open position of the slide;
on a side of the slide that faces the strand a protrusion is provided on said slide and arranged in such a way that upon displacement of the slide into the closed position, before assuming the closed position, it first abuts the lateral surface of the strand, before the slide can assume the closed position, by the protrusion passing the strand and deforming the elastically or elastomerically yielding plug while passing the strand;
sufficient space is available on opposite sides of the protrusion, in order to accommodate a section of the strand protruding from the elongated recess;
a second stop is provided on the bracket and the slide abuts said second stop in the closed position, once the protrusion has passed the strand.

2. The bracket according to claim 1, wherein a length of the elongated recess is smaller than a width of the slide.

3. The bracket according to claim 1, wherein the strand rests in the gingival or in the occlusal wall of the bracket and the second stop is formed on the wall of the bracket opposite to the wall where the strand rests.

4. The bracket according to claim 1, wherein the slide abuts the second stop with a front end of the slide.

5. The bracket according to claim 1, wherein the strand is provided in the gingival wall and the second stop is provided on the occlusal wall.

6. The bracket according to claim 1, wherein the strand protrudes from the opening of the recess at most with a semi-periphery of the strand.

7. The bracket according to claim 1, wherein the strand rests in the recess with more than a semi-periphery of the strand.

8. The bracket according to claim 1, wherein the strand rests in the elongated recess without lateral play.

9. The bracket according to claim 1, wherein the opening of the recess extends from the base.

10. The bracket according to claim 1, wherein the recess extends vertically with respect to the slide.

11. The bracket according to claim 1, wherein the slide is a flat structure.

12. The bracket according to claim 1, wherein the strand rests in the elongated recess loosely or held by friction.

13. The bracket according to claim 1, wherein the strand consists of a ceramic material.

14. The bracket according to claim 1, wherein the base, the occlusal wing and the gingival wing consist of a ceramic material.

15. The bracket according to claim 14, wherein the ceramic material is aluminium oxide.

16. The bracket according to claim 14, wherein the ceramic material is aluminium oxide, whereas the slide consists of a ceramic material with greater strength than aluminium oxide.

17. The bracket according to claim 14, wherein the slide consists of zirconium oxide.

18. The bracket according to claim 1, wherein the elongated recess is in the shape of a slit, which extends from the opening facing the slide continuously up to an underside of the base and the plug, on which the strand is supported, is inserted in the slit.

19. The bracket according to claim 18, wherein the slit has a cross-section which is totally occupied by the plug.

20. The bracket according to claim 19, wherein the plug is glued in the slit.

21. The bracket according to claim 18, wherein the plug has grooves which run in a direction from the base to the slide.

22. The bracket according to claim 18, wherein the plug consists of synthetic material.

23. The bracket according to claim 18, wherein the plug is stepped in such a way that it only partially fills up a cross-section of the recess in close vicinity to the strand.

24. The bracket according to claim 1, wherein the protrusion is wedge-shaped.

25. The bracket according to claim 24, wherein a surface of the wedge-shaped protrusion, which faces the strand in the closed position, runs more steeply than a surface of the wedge-shaped protrusion which points to a direction opposite the strand.

26. The bracket according to claim 1, wherein the slide has rounded external rims, which in the closed position of the slide faces a bottom of the slot.

27. The bracket according to claim 1, wherein the slot has rounded external edges.

28. The bracket according to claim 1, wherein the slide comprises at least one depression on an upper side of the slide.

29. The bracket according to claim 28, wherein said at least one depression has a tapered shape.

30. The bracket according to claim 1, wherein the slide has, on an upper side of the slide, two depressions lying one after another in the displacement direction of the slide.

* * * * *